(12) United States Patent
Assif

(10) Patent No.: US 11,112,473 B2
(45) Date of Patent: Sep. 7, 2021

(54) SYSTEMS AND METHODS FOR AVOIDING MRI-ORIGINATED INTERFERENCE WITH CONCURRENTLY USED SYSTEMS

(71) Applicant: Benny Assif, Ramat HaSharon (IL)

(72) Inventor: Benny Assif, Ramat HaSharon (IL)

(73) Assignee: INSIGHTEC, LTD., Tirat Carmel (IL)

( * ) Notice: Subject to any disclaimer, the term of this patent is extended or adjusted under 35 U.S.C. 154(b) by 1247 days.

(21) Appl. No.: 14/883,785

(22) Filed: Oct. 15, 2015

(65) Prior Publication Data

US 2016/0033601 A1 Feb. 4, 2016

Related U.S. Application Data

(63) Continuation-in-part of application No. 13/222,086, filed on Aug. 31, 2011, now abandoned.

(51) Int. Cl.
*G01R 33/48* (2006.01)
*A61B 8/00* (2006.01)
(Continued)

(52) U.S. Cl.
CPC .......... *G01R 33/4814* (2013.01); *A61B 5/055* (2013.01); *A61B 8/4416* (2013.01);
(Continued)

(58) Field of Classification Search
CPC ............ G01R 33/4814; A61B 8/4416; A61B 5/7217; A61B 5/055; A61B 7/02;
(Continued)

(56) References Cited

U.S. PATENT DOCUMENTS 6,278,890 B1 * 8/2001 Chassaing ................ A61B 7/00
600/407
6,735,461 B2 5/2004 Vitek et al.
(Continued)

FOREIGN PATENT DOCUMENTS

JP 2004209066 A * 7/2004

OTHER PUBLICATIONS

Curiel, Laura, Rajiv Chopra, and Kullervo Hynynen. "Progress in multimodality imaging: truly simultaneous ultrasound and magnetic resonance imaging." IEEE transactions on medical imaging 26.12 (2007): 1740-1746. (Year: 2007).*
(Continued)

*Primary Examiner* — Sean D Mattson
(74) *Attorney, Agent, or Firm* — Morgan, Lewis & Bockius LLP

(57) ABSTRACT

MRI interference with a concurrently operated system may be reduced or corrected by subtracting the MRI interference from signals measured using the concurrently operated system. Various approaches for performing MRI of an anatomic region in conjunction with a radio-frequency-sensitive (RF-sensitive) measurement of the region using the concurrently operated system include the steps of simultaneously performing an MR scan sequence including MR pulses and the RF-sensitive measurements; recording the RF-sensitive measurements as they are made; detecting intervals during the MR scan sequence when an RF level is sufficient to interfere with the RF-sensitive measurements; and retaining only the RF-sensitive measurements performed outside the detected intervals.

7 Claims, 10 Drawing Sheets

(51) Int. Cl.
  *A61N 7/02* (2006.01)
  *A61B 5/055* (2006.01)
  *A61B 17/22* (2006.01)
  *A61B 8/08* (2006.01)
  *A61N 7/00* (2006.01)
  *A61B 90/00* (2016.01)

(52) U.S. Cl.
  CPC .............. *A61N 7/02* (2013.01); *A61B 8/0808* (2013.01); *A61B 8/4444* (2013.01); *A61B 8/4488* (2013.01); *A61B 8/481* (2013.01); *A61B 2017/22007* (2013.01); *A61B 2090/374* (2016.02); *A61B 2090/378* (2016.02); *A61N 2007/0078* (2013.01)

(58) Field of Classification Search
  CPC ..... A61B 8/481; A61B 8/0808; A61B 8/4488; A61B 8/4444; A61B 2090/378; A61B 2090/374; A61B 2017/22007; A61N 2007/0078
  See application file for complete search history.

(56) References Cited

U.S. PATENT DOCUMENTS

| | | | | |
|---|---|---|---|---|
| 2001/0049474 | A1* | 12/2001 | Wagshul | A61B 5/055 600/411 |
| 2002/0193681 | A1* | 12/2002 | Vitek | G01R 33/28 600/411 |
| 2004/0267111 | A1* | 12/2004 | Feinberg | A61B 8/08 600/411 |
| 2013/0053678 | A1 | 2/2013 | Vitek et al. | |

OTHER PUBLICATIONS

Ochi et al. (JP 2004209066) Human Translation produced Schreiber Translations, Inc. Apr. 2020. (Year: 2020).*

Auboirous, et al., "Ultrasonography-Based 2D Motion-Compensated HIFU Sonication Integrated with Reference-Free MR Temperature Monitoring: A Feasibility Study ex vino", 2012, Phys. Med. Bio., vol. 57, pp. N159-N171.

Curiel, et al., "Progress in Multimodality Imaging: Truly Simultaneous Untrasound and Magnetic Resonance Imaging", IEEE Transactions on Medical Imaging, 2007, vol. 26, No. 12, pp. 1740-1746.

Delannoy, et al., Hyperthermia System Combined with a Magnetic Resonance Imaging Unit, 1991, Medical Physics, vol. 17, No. 5, pp. 856-859.

Sebok, et al., "Interleaved Magnetic Resonance and Ultrasound by Electric Synchronization", Invest Radiol, 1991, vol. 26, pp. 353-357.

International Search Report, International Patent No. PCT/US16/56833, dated Jan. 25, 2017, 15 pages.

* cited by examiner

SYSTEMS AND METHODS FOR AVOIDING MRI-ORIGINATED INTERFERENCE WITH CONCURRENTLY USED SYSTEMS

CROSS-REFERENCE TO RELATED APPLICATION

This application is a continuation-in-part of U.S. Ser. No. 13/222,086, filed on Aug. 31, 2011, the entire disclosure of which is hereby incorporated by reference.

FIELD OF THE INVENTION

The present invention relates, generally, to medical diagnosis and treatment methods guided by magnetic resonance imaging (MRI), and, more specifically, to approaches to minimizing MRI-induced interference.

BACKGROUND

Magnetic resonance imaging may be used in conjunction with ultrasound focusing in a variety of medical applications. Ultrasound penetrates well through soft tissues and, due to its short wavelengths, can be focused to spots with dimensions of a few millimeters. As a consequence of these properties, ultrasound can be and has been used for various diagnostic and therapeutic medical purposes, including ultrasound imaging and non-invasive surgery. For example, focused ultrasound may be used to ablate diseased (e.g., cancerous) tissue without causing significant damage to surrounding healthy tissue. An ultrasound focusing system generally utilizes an acoustic transducer surface, or an array of transducer surfaces, to generate an ultrasound beam. In transducer arrays, the individual surfaces, or "elements," are typically individually controllable—i.e., their vibration phases and/or amplitudes can be set independently of one another—allowing the beam to be steered in a desired direction and focused at a desired distance. The ultrasound system often also includes receiving elements, integrated into the transducer array or provided in form of a separate detector, that help monitor the focused ultrasound treatment, primarily for safety purposes. For example, the receiving elements may serve to detect ultrasound reflected off interfaces between the transducer and the target tissue, which may result from air bubbles on the skin that need to be removed to avoid skin burns. The receiving elements may also be used to detect cavitation in overheated tissues (i.e., the formation of cavities due to the collapse of bubbles formed in the liquid of the tissue).

To visualize the target tissue and guide the ultrasound focus during therapy, magnetic resonance imaging may be used. In brief, MRI involves placing a subject, such as the patient, into a homogeneous static magnetic field, thus aligning the spins of hydrogen nuclei in the tissue. Then, by applying a radio-frequency (RF) electromagnetic pulse of the right frequency (the "resonance frequency"), the spins may be flipped, temporarily destroying the alignment and inducing a response signal. Different tissues produce different response signals, resulting in a contrast among theses tissues in MR images. Because the resonance frequency and the frequency of the response signal depend on the magnetic field strength, the origin and frequency of the response signal can be controlled by superposing magnetic gradient fields onto the homogeneous field to render the field strength dependent on position. By using time-variable gradient fields, MRI "scans" of the tissue can be obtained. Many MRI protocols utilize time-dependent gradients in two or three mutually perpendicular directions. The relative strengths and timing of the gradient fields and RF pulses are specified in a pulse sequence and may be illustrated in a pulse sequence diagram.

Time-dependent magnetic field gradients may be exploited, in combination with the tissue dependence of the MRI response signal, to visualize, for example, a brain tumor, and determine its location relative to the patient's skull. An ultrasound transducer system, such as an array of transducers attached to a housing, may then be placed on the patient's head. The ultrasound transducer may include MR tracking coils or other markers that enable determining its position and orientation relative to the target tissue in the MR image. Based on computations of the required transducer element phases and amplitudes, the transducer array is then driven so as to focus ultrasound into the tumor. Alternatively or additionally, the ultrasound focus itself may be visualized, using a technique such as thermal MRI or acoustic resonance force imaging (ARFI), and such measurement of the focus location may be used to adjust the focus position. These methods are generally referred to as magnetic-resonance-guided focusing of ultrasound (MRgFUS).

In addition, an MRI apparatus and an ultrasound imaging system may be combined to offer the strengths of both imaging modalities and thereby provide novel insights into the morphology and function of normal and diseased tissues. MRI is used widely for both diagnostic and therapeutic applications because of its multi-planar imaging capability, high signal-to-noise ratio, and sensitivity to subtle changes in soft tissue morphology and function. Ultrasound imaging, on the other hand, has advantages including high temporal resolution, high sensitivity to acoustic scatters (such as calcifications and gas bubbles), excellent visualization, and measurement of blood flow, low cost, and portability. Benefits of combining these complementary modalities have been shown in intraoperative neurosurgical applications and breast biopsy guidance. By performing imaging with both modalities simultaneously, a number of issues such as spatial and temporal registration between data sets may be simplified. In addition, measurements of unique physiological parameters can be made with each modality to fully characterize the organ or tissue under evolution.

The simultaneous operation of ultrasound and MRI apparatus, however, can lead to undesired interferences. For example, MRI is very sensitive to RF noise generated by the focused ultrasound system (see, e.g., U.S. Pat. No. 6,735, 461). Conversely, focused ultrasound procedures often involve RF-sensitive operations (such as the ultrasound detection that may accompany treatment with focused ultrasound) that are easily disturbed by RF excitation signals and/or time-varying field gradient generated by the MRI system. Prior-art approaches to avoiding such interference typically involve shielding. Shielding the ultrasound system from interfering MR signals typically requires covering or surrounding the whole transducer and associated cables in metallic shield. In some systems, however, acoustic constraints prevent complete encapsulation of the ultrasound-receiving elements, resulting in penetration of, e.g., the front layer of a receiver and/or the cables by some amount of RF noise. Accordingly, there is a need for alternative approaches in MRgFUS applications to minimize or avoid interferences between the two systems.

SUMMARY

Embodiments of the present invention provide various approaches to simultaneously operating an MRI apparatus for imaging an anatomic region and a system for concurrently performing RF-sensitive operations without or with reduced MRI interference. The concurrently operated system may be any system or sensor that has diagnostic and therapeutic applications. For example, it may be a treatment system (such as a phased-array ultrasound transducer system), an imaging system (such as an ultrasound imaging probe) or a signal-detection sensor (such as an ultrasonic cavitation sensor). In various embodiments, the MR interference originating from excitation of the MRI apparatus is first measured by the signal-detection sensor and/or detection channel(s) associated with the concurrently operated system when the latter system is idling—i.e., inactive or not actively transmitting energy (e.g., acoustic energy), while the MRI apparatus is normally operated (to perform "cold" scans, i.e., scans that are not concurrent with treatment, ultrasound imaging, or cavitation detections). Because MR interference is typically an additive, stationary noise with respect to the desired signal, signal(s) measured by the concurrently operated system when both it and an MRI apparatus are simultaneously active (i.e., performing "hot" scans) can be corrected by subtracting the MR interference measured during cold scans from the measured signal(s) obtained during hot scans. Accordingly, embodiments of the present invention correct signals measured by the concurrently operated system so that they are not significantly distorted by MR interference; this is advantageous in that it generally eliminates the need for shielding the RF signals as required by the prior art.

In some embodiments, a Fast Fourier Transform (FFT) approach is used to convert the measured RF-sensitive signal(s) and MR interference to the frequency domain. Subtraction of the MR interference from the measured signal(s) can then be performed on the converted signals at each frequency in the spectrum. This is particularly useful when the measured signal(s) of the concurrently operated system are insensitive to the phase measurements (e.g., cavitation measurements) and can thereby avoid the need to accurately synchronize operations of the MRI apparatus and the concurrently operated system.

If, during operation, the concurrently operated system is at least partially synchronized with the MRI scanning (i.e., synchronized only within one or more time windows), the signal(s) measured by the concurrently operated system may be corrected by identifying the MR interference within the time window(s) and subtracting the MR interference therefrom. In some embodiments, the MR interference is pseudo-stationary for each repetition time (or time to repeat (TR)); accordingly, the MR interference obtained during the cold scans can be reduced to a single set of data. The single set of MR interference data may correspond to, for example, a single cold scan TR, an average of MR interference recorded during multiple cold scan TRs, or a maximum MR interference in the multiple cold scan TRs. This approach can reduce complexity when processing a massive data volume representing MR interference and signal(s) acquired during simultaneous operation of the MRI apparatus and the RF-sensitive system.

Accordingly, in one aspect, the invention pertains to a method of performing magnetic resonance (MR) imaging of an anatomic region in conjunction with a radio-frequency-sensitive (RF-sensitive) measurement of the region using a concurrently operated system (such as a phased-array ultrasound transducer system, an ultrasound imaging probe, and/or a cavitation sensor). In various embodiments, the method includes the steps of: with the concurrently operated system idle, performing an MR scan sequence including MR pulses; detecting intervals during the MR scan sequence when an RF level is sufficient to interfere with the RF-sensitive measurements; storing data indicative of a temporal extent of the MR scan sequence and the detected intervals thereduring; and based at least in part on the stored data, simultaneously performing the scan sequence and operating the concurrently operated system but obtaining the RF-sensitive measurements only during times not corresponding to the recorded intervals. The detecting step may be performed by the concurrently operated system and/or one or more dedicated sensors outside the concurrently operated system. The MR scan sequence may be performed periodically and the RF-sensitive measurements may be performed at least partially in synchronization with at least one of the MR scan sequence.

In another aspect, the invention relates to a system for performing MR imaging of an anatomic region in conjunction with a RF-sensitive measurement of the region. In various embodiments, the system includes an MR imaging apparatus for imaging the anatomic region; a concurrently operated system for performing the RF-sensitive measurement; and a controller in communication with the MR imaging apparatus and the concurrently operated system. In one implementation, the controller is configured to: with the concurrently operated system idle, perform an MR scan sequence including MR pulses; determine intervals during the MR scan sequence when an RF level is sufficient to interfere with the RF-sensitive measurements; store data indicative of a temporal extent of the MR scan sequence and the detected intervals thereduring; based at least in part on the stored data, simultaneously perform the scan sequence and operate the concurrently operated system but obtain the RF-sensitive measurements only during times not corresponding to the recorded intervals. The determination of the intervals may be performed by the concurrently operated system and/or one or more dedicated sensors outside the concurrently operated system. In various embodiments, the controller is further configured to: (i) perform the MR scan sequence periodically; and (ii) perform the RF-sensitive measurements at least partially in synchronization with one or more MR scan sequences.

Another aspect of the invention relates to a method of performing MR imaging of an anatomic region in conjunction with a RF-sensitive measurement of the region using a concurrently operated system. In various embodiments, the method includes the steps of: simultaneously performing an MR scan sequence including MR pulses and the RF-sensitive measurements; recording the RF-sensitive measurements as they are made; detecting intervals during the MR scan sequence when an RF level is sufficient to interfere with the RF-sensitive measurements; and retaining only the RF-sensitive measurements performed outside the detected intervals. The detecting step may be performed by the concurrently operated system and/or by one or more dedicated sensors outside the concurrently operated system.

In yet another aspect, the invention pertains to a method of performing MR imaging of an anatomic region in conjunction with a RF-sensitive measurement of the region using a concurrently operated system. In various embodiments, the method includes the steps of: simultaneously performing an MR scan sequence including MR pulses and obtaining the RF-sensitive measurements; recording the RF-sensitive measurements as they are made; detecting intervals during the MR scan sequence when an RF level is sufficient to interfere with the RF-sensitive measurements and recording the detected RF levels during the intervals; and adjusting the recorded RF-sensitive measurements that were obtained during the detected intervals based on the recorded RF levels. The detecting step may be performed by the concurrently operated system and/or by one or more dedicated sensors outside the concurrently operated system.

Still another aspect of the invention relates to a system for performing MR imaging of an anatomic region in conjunction with a RF-sensitive measurement of the region. In various embodiments, the system includes: an MR imaging apparatus for imaging the anatomic region; a concurrently operated system for performing the RF-sensitive measurement; and a controller in communication with the MR imaging apparatus and concurrently operated system. In one implementation, the controller is configured to: simultaneously perform an MR scan sequence including MR pulses and the RF-sensitive measurements; record the RF-sensitive measurements as they are made; determine intervals during the MR scan sequence when an RF level is sufficient to interfere with the RF-sensitive measurements; and retain only the RF-sensitive measurements performed outside the detected intervals. The determination of the intervals may be performed by the concurrently operated system and/or by one or more dedicated sensors outside the concurrently operated system.

In another aspect, the invention relates to a system for performing MR imaging of an anatomic region in conjunction with a RF-sensitive measurement of the region. In some embodiments, the system includes: an MR imaging apparatus for imaging the anatomic region; a concurrently operated system for performing the RF-sensitive measurement; and a controller in communication with the MR imaging apparatus and concurrently operated system. In various embodiments, the controller is configured to: simultaneously perform an MR scan sequence including MR pulses and obtaining the RF-sensitive measurements; record the RF-sensitive measurements as they are made; determine intervals during the MR scan sequence when an RF level is sufficient to interfere with the RF-sensitive measurements and record the detected RF levels during the intervals; and adjust the recorded RF-sensitive measurements that were obtained during the detected intervals based on the recorded RF levels. The determination of the intervals may be performed by the concurrently operated system and/or by one or more dedicated sensors outside the concurrently operated system.

In still another aspect, the invention relates to a method of performing MR imaging of an anatomic region in conjunction with a RF-sensitive measurement of the region using a concurrently operated system. In various embodiments, the method includes the steps of: with the concurrently operated system idle, performing an MR scan sequence including MR pulses; detecting intervals during the MR scan sequence when a level of RF noise is sufficient to interfere with the RF-sensitive measurements; detecting a parameter of the RF noise during the intervals and recording the detected parameter; storing data indicative of a temporal extent of the MR scan sequence and the detected intervals and parameter of the RF noise thereduring; simultaneously performing an MR scan sequence including MR pulses and obtaining the RF-sensitive measurements; recording the RF-sensitive measurements as they are made; and adjusting the recorded RF-sensitive measurements that were obtained during the detected intervals based on the recorded RF levels.

The adjustment may correspond to subtracting the recorded RF levels from the recorded RF-sensitive measurements that were obtained during the detected intervals. In addition, the detected parameter may be a spectrum of the RF noise and the subtracting step may include, for each RF-sensitive measurement, obtaining a spectrum of a signal corresponding to the measurement and subtracting, at each frequency in the spectra, a magnitude of the RF noise from a magnitude of the signal corresponding to the measurement. The spectra may be obtained from time-domain signal measurements using a Fast Fourier Transform. In one embodiment, the detected parameter is a maximum level of the RF noise during an interval and the subtracting step includes subtracting the maximum RF noise from the corresponding recorded RF-sensitive measurement. In another embodiment, the detected parameter is an average level of the RF noise and the subtracting step includes subtracting the average RF noise from each recorded RF-sensitive measurement.

In some embodiments, the MR scan sequence is performed periodically and the RF-sensitive measurements are performed at least partially in synchronization with one or more MR scan sequences. Additionally, the method further includes determining time windows of the RF-sensitive measurements and identifying the RF noise within the determined time windows; adjustment of the recorded RF-sensitive measurements corresponds to subtracting the identified RF noise from the recorded RF-sensitive measurements that were obtained during the detected time windows.

In another aspect, the invention pertains to a system for performing MR imaging of an anatomic region in conjunction with a RF-sensitive measurement of the region. In various embodiments, the system includes: an MR imaging apparatus for imaging the anatomic region; a concurrently operated system for performing the RF-sensitive measurement; and a controller in communication with the MR imaging apparatus and concurrently operated system. In one implementation, the controller is configured to: with the concurrently operated system idle, perform an MR scan sequence including MR pulses; determine intervals during the MR scan sequence when a level of RF noise is sufficient to interfere with the RF-sensitive measurements; determine a parameter of the RF noise during the intervals and record the detected parameter; store data indicative of a temporal extent of the MR scan sequence and the detected intervals and parameter of the RF noise thereduring; simultaneously perform an MR scan sequence including MR pulses and obtain the RF-sensitive measurements; record the RF-sensitive measurements as they are made; and adjust the recorded RF-sensitive measurements that were obtained during the detected intervals based on the recorded RF levels.

The adjustment may correspond to subtracting the recorded RF levels from the recorded RF-sensitive measurements that were obtained during the detected intervals. In addition, the detected parameter may be a spectrum of the RF noise and the controller may be further configured to, for each RF-sensitive measurement, obtain a spectrum of a signal corresponding to the measurement and subtract, at each frequency in the spectra, a magnitude of the RF noise from a magnitude of the signal corresponding to the measurement. The spectra may be obtained from time-domain signal measurements using a Fast Fourier Transform. In one embodiment, the detected parameter is a maximum level of the RF noise during an interval and the controller is further configured to subtract the maximum RF noise from the corresponding recorded RF-sensitive measurement. In another embodiment, the detected parameter is an average level of the RF noise and the controller is further configured to subtract the average RF noise from each recorded RF-sensitive measurement.

In various embodiments, the controller is further configured to: (i) perform the MR scan sequence periodically; and (ii) perform the RF-sensitive measurements at least partially in synchronization with one or more MR scan sequences. Additionally, the controller is further configured to: determine time windows of the RF-sensitive measurements; and identify the RF noise within the determined time windows; adjustment of the recorded RF-sensitive measurements corresponds to subtracting the identified RF noise from the recorded RF-sensitive measurements that were obtained during the detected time windows.

As used herein, the terms "approximately," "roughly," and "substantially" mean ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
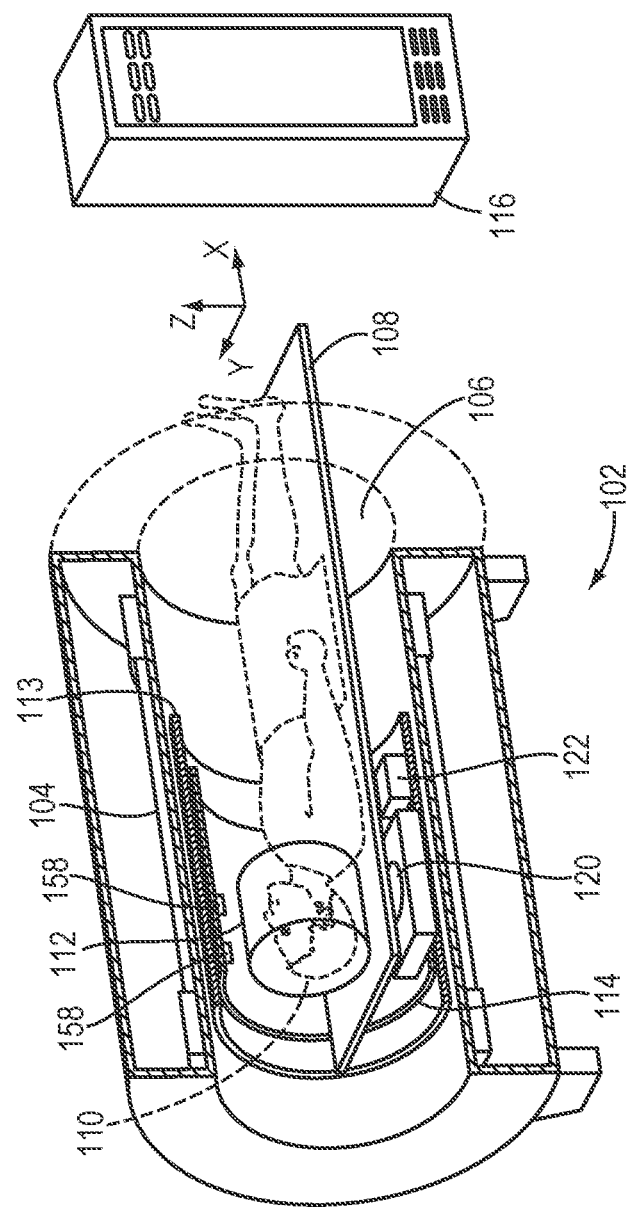
FIG. 1A schematically depicts an exemplary MRI system in accordance with various embodiments of the current invention.

FIG. 1A illustrates an exemplary MRI apparatus or system 102. The apparatus 102 may include a cylindrical electromagnet 104, which generates the requisite static magnetic field within a bore 106 of the electromagnet 104. During medical procedures, a patient is placed inside the bore 106 on a movable support table 108. A region of interest 110 within the patient (e.g., the patient's head) may be positioned within an imaging region 112 wherein the electromagnet 104 generates a substantially homogeneous field. A set of cylindrical magnet field gradient coils 113 may also be provided within the bore 106 and surrounding the patient. The gradient coils 113 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 114 surrounding the imaging region 112 emits RF pulses into the imaging region 112 to cause the patient's tissues to emit magnetic-resonance (MR) response signals. Raw MR response signals are sensed by the RF coil 114 and passed to an MR controller 116 that then computes an MR image, which may be displayed to the user. Alternatively, separate MR transmitter and receiver coils may be used. Images acquired using the MRI apparatus 102 may provide radiologists and physicians with a visual contrast between different tissues and detailed internal views of a patient's anatomy that cannot be visualized with conventional x-ray technology.

The MRI controller 116 may control the pulse sequence, i.e., the relative timing and strengths of the magnetic field gradients and the RF excitation pulses and response detection periods. The MR response signals are amplified, conditioned, and digitized into raw data using an image processing system, and further transformed into arrays of image data by methods known to those of ordinary skill in the art. Based on the image data, a treatment region (e.g., a tumor) is identified. The image processing system may be part of the MRI controller 116, or may be a separate device (e.g., a general-purpose computer containing image processing software) in communication with the MRI controller 116. In some embodiments, one or more ultrasound systems 120 or one or more sensors 122 are displaced within the bore 106 of the MRI apparatus 102 as further described below.

Figure 1B:
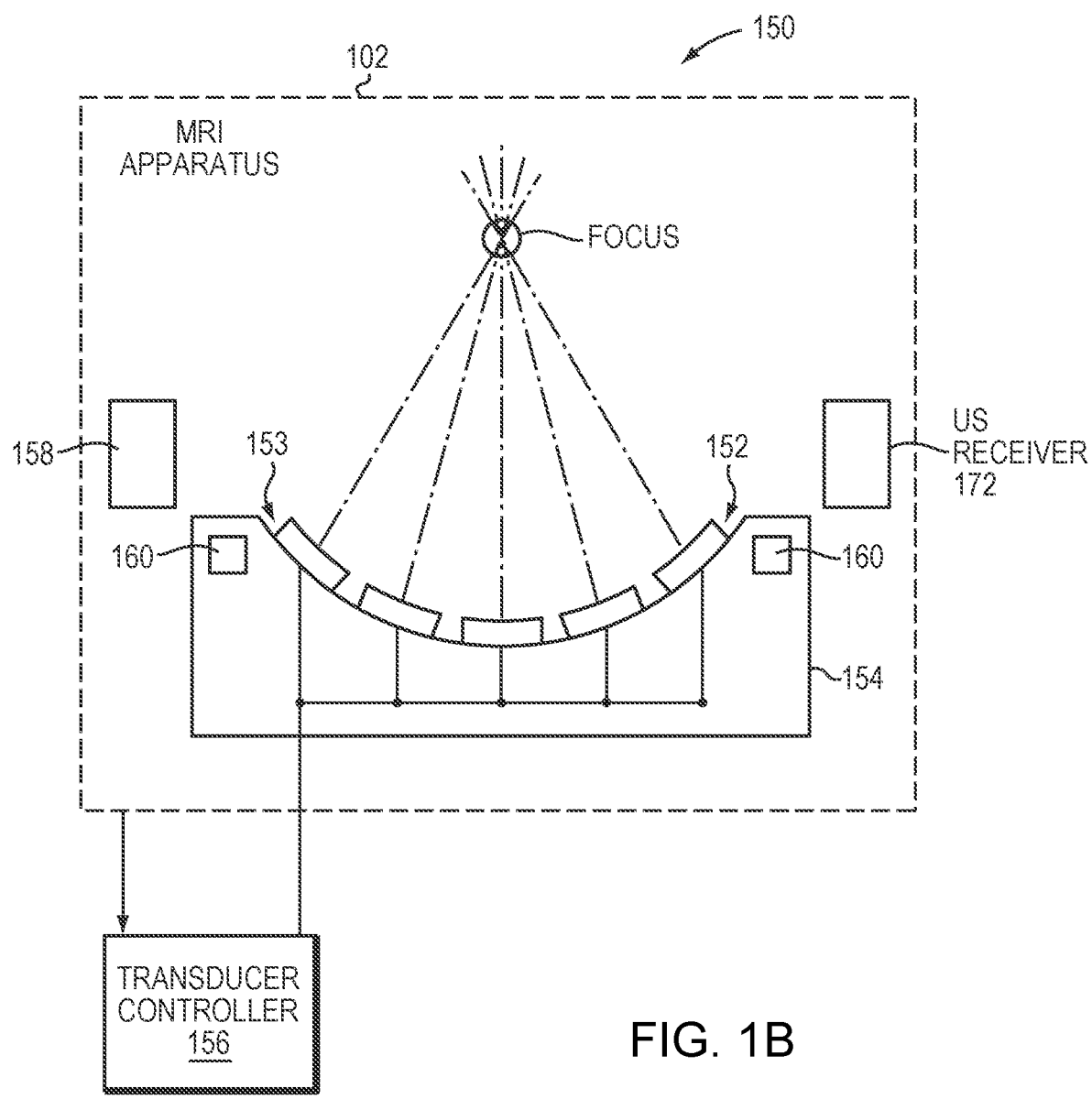
FIG. 1B schematically depicts an exemplary system (e.g., focused ultrasound system) concurrently operated with the MRI system in accordance with various embodiments of the current invention.

FIG. 1B illustrates an exemplary system 150, such as an ultrasound system, concurrently operated with the MRI system 102 in accordance with some embodiments of the present invention, although alternative concurrently operated systems with similar or different functionality that may interfere with the MRI system 102 are also within the scope of the invention. As shown, the ultrasound system includes a plurality of ultrasound transducer elements 152, which are arranged in an array 153 at the surface of a housing 154. The array may comprise a single row or a matrix of transducer elements 152. In alternative embodiments, the transducer elements 152 may be arranged without coordination, i.e., they need not be spaced regularly or arranged in a regular pattern. The array may have a curved (e.g., spherical or parabolic) shape, as illustrated, or may include one or more planar or otherwise shaped sections. Its dimensions may vary, depending on the application, between millimeters and tens of centimeters. The transducer elements 152 may be piezoelectric ceramic elements. Piezo-composite materials, or generally any materials capable of converting electrical energy to acoustic energy, may also be used. To damp the mechanical coupling between the transducer elements 152, they may be mounted on the housing 154 using silicone rubber or any other suitable damping material.

The transducer elements 152 are separately controllable, i.e., they are each capable of emitting ultrasound waves at amplitudes and/or phases that are independent of the amplitudes and/or phases of the other transducers. A transducer controller 156 serves to drive the transducer elements 152. For n transducer elements, the transducer controller 156 may contain n control circuits each comprising an amplifier and a phase delay circuit, each control circuit driving one of the transducer elements. The transducer controller 156 may split an RF input signal, typically in the range from 0.1 MHz to 4 MHz, into n channels for the n control circuit. It may be configured to drive the individual transducer elements 152 of the array at the same frequency, but at different phases and different amplitudes so that they collectively produce a focused ultrasound beam. The transducer controller 156 desirably provides computational functionality, which may be implemented in software, hardware, firmware, hardwiring, or any combination thereof, to compute the required phases and amplitudes for a desired focus location. In general, the transducer controller 156 may include several separable apparatus, such as a frequency generator, a beamformer containing the amplifier and phase delay circuitry, and a computer (e.g., a general-purpose computer) performing the computations and communicating the phases and amplitudes for the individual transducer elements 152 to the beamformer. Such systems are readily available or can be implemented without undue experimentation.

To perform ultrasound imaging, the transducer controller 156 drives the transducer elements 152 to transmit acoustic signals into a region being imaged and to receive reflected signals from various structures and organs within the patient's body. By appropriately delaying the pulses applied to each transducer element 152, a focused ultrasound beam can be transmitted along a desired scan line. Acoustic signals reflected from a given point within the patient's body are received by the transducer elements 152 at different times. The transducer elements can then convert the received acoustic signals to electrical signals which are supplied to the beamformer. The delayed signals from each transducer element 152 are summed by the beamformer to provide a scanner signal that is a representation of the reflected energy level along a given scan line. This process is repeated for multiple scan lines to provide signals for generating an image of the prescribed region of the patient's body. Typically, the scan pattern is a sector scan, wherein the scan lines originate at the center of the ultrasound transducer and are directed at different angles. A linear, curvilinear or any other scan pattern can also be utilized.

In various embodiments, during a focused ultrasound procedure, small gas bubbles, or "micro-bubbles," are generated in the liquid contained in the tissue due to the stress resulting from negative pressure produced by the propagating ultrasonic waves and/or from when the heated liquid ruptures and is filled with gas/vapor. On one hand, the micro-bubbles have a positive treatment effect by generating higher harmonic frequencies of the original wave energy, thereby increasing the absorption of energy in the tissue. On the other hand, the reaction of tissue containing a higher relative percentage of micro-bubbles to the continued application of the ultrasound energy is non-linear and difficult to predict. For example, the micro-bubbles may collapse due to the applied stress from an acoustic field. This mechanism, called "cavitation," may cause extensive tissue damage beyond that targeted. Accordingly, to monitor the micro-bubbles in the target tissue when the acoustic waves are applied, in various embodiments, the concurrently operated system 150 includes one or more ultrasonic cavitation sensors 158. The cavitation sensor(s) 158 detects acoustic radiation that is emitted by the micro-bubbles due to a change of their volumes when driven by the external applied acoustic field. By analyzing the spectral characteristics of the detected acoustic radiation, detailed information regarding the dynamics of the cavitation process can be obtained. Because the acoustic signals emitted by the micro-bubbles are in an RF range, they are easily disturbed by RF excitation signals and/or time-varying field gradients generated by the MRI system 102. Accordingly, it is also critical to eliminate/avoid MR interference when detecting the cavitation signals.

The concurrently operated system 150, such as the ultrasound system and/or cavitation sensor(s), may be disposed within the bore 106 of the MRI apparatus 102 or placed in the vicinity of the MRI apparatus 102. For example, multiple cavitation sensors 158 may be provided to surround the imaging region 112. To aid in determining the relative position of the concurrently operated system 150 and MRI apparatus 102, the concurrently operated system 150 may further include MR trackers 160 associated therewith, arranged at a fixed position and orientation relative to the concurrently operated system 150. The trackers 160 may, for example, be incorporated into or attached to the concurrently operated system housing. If the relative positions and orientations of the MR trackers 160 and concurrently operated system 150 are known, MR scans of the MR trackers 160 implicitly reveal the location of the concurrently operated system 150 in MRI coordinates, i.e., in the coordinate system of the MRI apparatus 102.

As depicted in FIGS. 1A and 1B, a combined system including the MRI apparatus 102 and concurrently operated system 150 may be capable of imaging the anatomic region of interest and detect ultrasound signals; the combined system may serve to monitor the application of ultrasound for treatment and/or safety purposes. For example, ultrasound reflections off tissue interfaces that intersect the ultrasound beam path may be analyzed to ensure, if necessary by adjustment of the treatment protocol, that such interfaces are not inadvertently overheated. Further, measurements of the received cavitation spectrum may be used to detect cavitation resulting from the interaction of ultrasound energy with water-containing tissue. In addition, the visualization of the tissue and target may be supplemented by ultrasound imaging, for example, to facilitate tracking a moving target. Ultrasound detection may be accomplished with the ultrasound transducer array 153. For example, treatment and imaging periods may be interleaved, or a contiguous portion of the array 153 or discontiguous subset of transducer elements 152 may be dedicated to imaging while the remainder of the array 153 focuses ultrasound for treatment purposes. Alternatively, a separate ultrasound receiver 172, which may be, e.g., a simple ultrasound probe or array of elements, may be provided. The separate receiver 172 may be placed in the vicinity of the ultrasound transducer array 153, or integrated into its housing 154. In addition, the receiver 172 may be disposed within the bore 106 of the MRI apparatus 102 or placed in the vicinity thereof.

Figure 2:
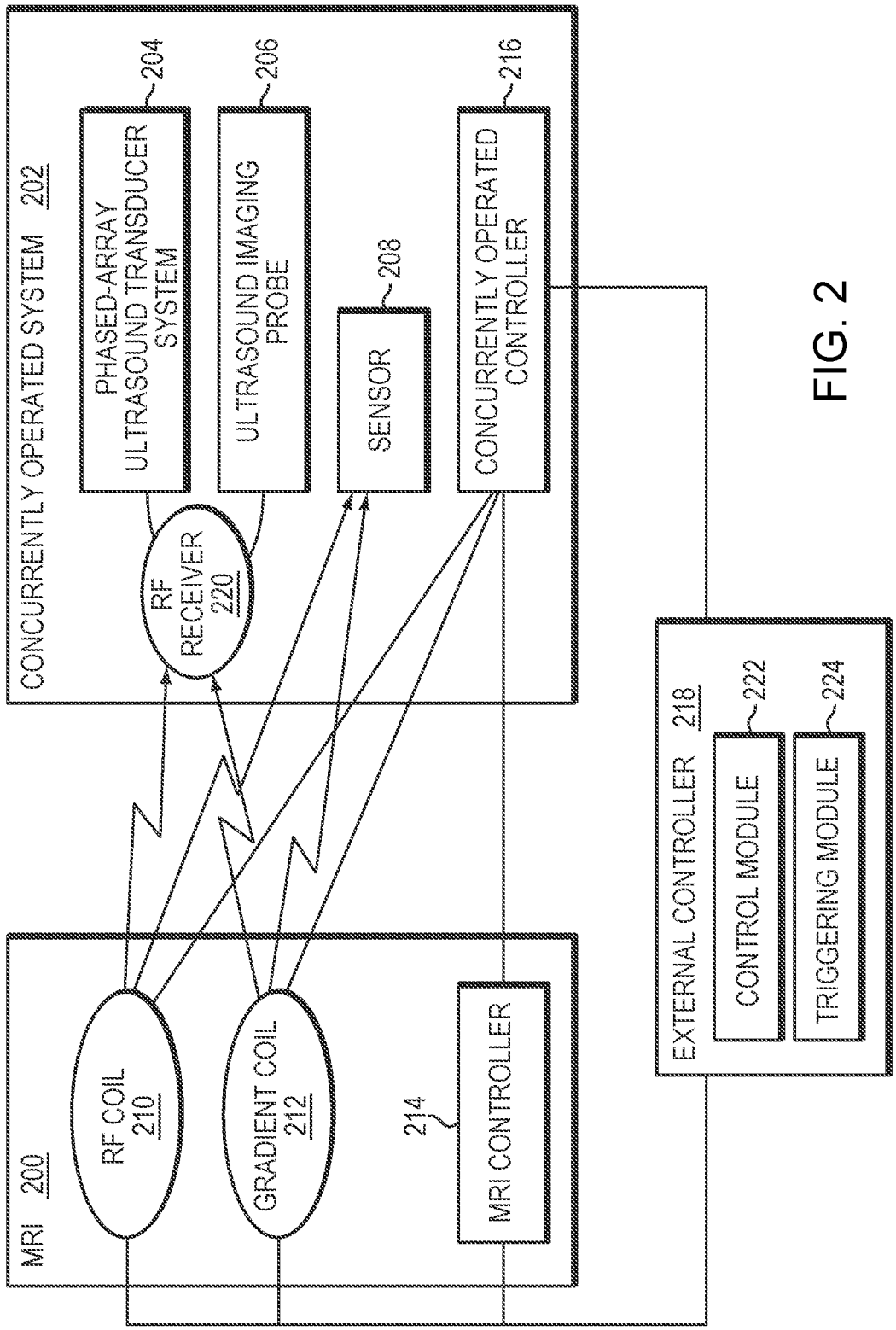
FIG. 2 schematically illustrates interactions between an MRI apparatus and a concurrently operated system in accordance with various embodiments of the current invention.

FIG. 2 schematically illustrates the interaction between an MRI apparatus 200 and a concurrently operated system 202, such as a phased-array ultrasound transducer system 204, an ultrasound imaging probe 206, or a separate, dedicated RF sensor (such as a cavitation sensor) 208, in accordance with various embodiments of the invention. The MRI apparatus 200 includes RF transmitter coils 210 and gradient coils 212 for generating time-varying magnetic gradients across the tissue to be imaged. Both transmitter-coil and gradient-coil emissions fall in the RF range and can potentially disturb ultrasonic treatment/imaging procedures and/or cavitation detections (or other concurrently performed RF-sensitive operations). The MRI transmitter coils 210 generate electromagnetic pulses with frequencies in the range from about 50 MHz to about 150 MHz to induce spin flipping. The gradients generated by the gradient coils 212 are typically updated at kHz or MHz frequencies, and are substantially constant between successive updates. For example, the gradient value (i.e., the magnetic field strength of the gradient field) may be controlled digitally at a sampling rate of 250 kHz by applying a new current every four microseconds. These small control steps generate RF noise, mainly at the sampling frequency (i.e., 250 kHz in the example) and its harmonics (i.e., 500 kHz, 750 kHz, etc.). A step in the gradient value is usually implemented by a controlled ramp whose slope is proportional to the current step. The resulting RF noise is generally proportional to the current step as well. However, even during nominally static gradients, control steps exist and resulting in some level of RF noise (although significantly less than is generated during ramps). In other words, non-zero static gradients are quieter than dynamic gradients, but are not completely quiet.

Ultrasound imaging and measuring the cavitation spectrum of the acoustic reflections generally have low associated signal voltages (e.g., voltages in the 5 mV range and below). During these measurements, the ultrasound receiver (which may be the transducer array 153 operated in a "listening" mode, or a separate, dedicated receiver device 172) and/or the separate, dedicated RF sensors 208 may convert the acoustic signals into electrical RF signals. Such signals can also be created by the RF disturbances from the MRI apparatus 200, resulting in unwanted signal components. Since the detected signals generally have lower power than, e.g., focused ultrasound ablation pulses, they are particularly sensitive to such perturbations.

Figure 3A:
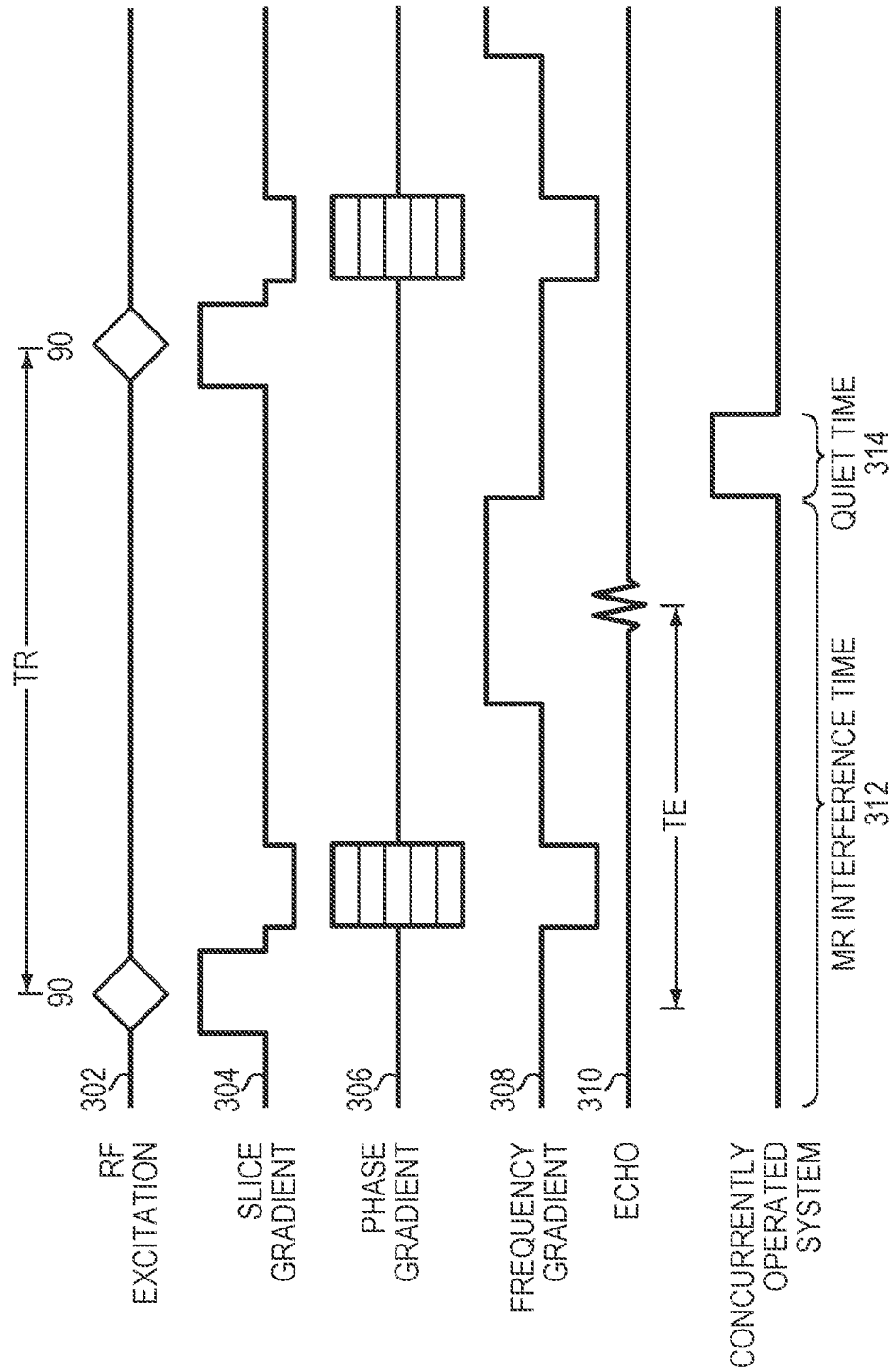
FIG. 3A is a pulse sequence diagram illustrating an exemplary MRI protocol as well as detection periods carried out by a concurrently operated system in accordance with various embodiments of the current invention.

FIG. 3A shows a pulse sequence diagram illustrating, for a typical MR gradient echo pulse sequence, the relative timing of the RF excitation pulse 302, the magnetic field gradients 304, 306, 308 in three directions, and the MR response signal 310, which occurs at the echo time (TE). The sequence may be periodically repeated; the period is denoted as the repetition time TR and may be, for example, in the range from 20 to 30 ms. FIG. 3 further shows the timing and the period during which operations of the concurrently operated system may be carried out. In some embodiments, if operations of the concurrently operated system are not especially sensitive to the RF disturbances (e.g., when performing focused ultrasound emissions for ablating the diseased tissue), they can be carried out at any time, including the period 312 during which the MRI gradients are active. If, however, the concurrently operated system is RF-sensitive, the detections are carried out during gradient idle times (or "quiet times") 314 of the MRI system—i.e., time intervals in which magnetic field gradients, or time variations thereof, are substantially unchanged and/or RF signals are not excited. In other words, operations of the MRI system 200 and the concurrently operated system 202 are synchronized based on the MRI pulse sequence that is computed and controlled by the MR controller 214. For example, during the MR idle time 314, the MRI apparatus 200 may send a synchronization signal to a controller 216 of the concurrently operated system 202, which can then perform spectrum measurements and/or other RF-sensitive operations.

Alternatively, synchronization may be effected through external control mechanisms. For example, referring again to FIG. 2, the controller module 216 of the concurrently operated system 202 and/or an external controller 218 may control the timing of RF-sensitive operations directly or via the MR controller 214 based on measurements of RF signals originating from the MRI apparatus 200. For example, the external controller 218 may communicate with the MRI and concurrently operated systems that each include individual controllers. The external controller 218 may include a control module 222 that determines when gradient-field activity is quiet, e.g., based on information received about an MRI pulse sequence specifying time intervals during which the gradients are quiet. The control module 222 may also send control signals to the MR controller 214 to stop MRI operation at the end of a sequence in order to create quiet time. The control module 222 may communicate gradient idle time to a triggering module 224 responsible for initiating the RF-sensitive measurement operation. The controllers 216, 218 are in communication with, for example, one or more RF receivers (such as ultrasound channels) 220 associated with the phased-array ultrasound transducer system 204 or ultrasound imaging probe 206 and/or by the separate, dedicated RF sensors 208 for performing RF-sensitive signal measurements during the gradient idle times 314. In some embodiments, the MR controller 214 and the controller 216 of the concurrently operated system 202 may be integrated into a single control module that sends synchronization or clock signals simultaneously to both apparatus 200, 202, or controls the RF transmitter coils 210, gradient coils 212, and concurrently operated system 202 directly.

In various embodiments, the gradient idle times 314 of the MRI system 200 are determined based on signals measured by the RF receiver(s) 220 associated with the phased-array ultrasound transducer system 204 or ultrasound imaging probe 206 and/or by the separate, dedicated RF sensor(s) 208. In one embodiment, the MRI system 200 is activated to perform standard operations while the concurrently operated system 202 is idling—i.e., the concurrently operated system 202 is inactive or not performing at least one of its functions (such as emitting acoustic waves) but is capable of detecting signals transmitted (this process is denoted as a "cold" scan). Accordingly, the time periods during which the RF signals can be detected by the RF receiver(s) 220 and/or RF sensor(s) 208 are defined as gradient-active times, whereas the time periods during which the detected RF signals are below a threshold are defined as gradient-idle times. The threshold may be a level that would interfere with RF-sensitive operations. The gradient-active and gradient-idle times are defined against the period of the scan or a repeating portion thereof. Thus, because the pulse sequence is recurring, the gradient-active and gradient-idle time intervals of the MRI pulse sequence may be "learned" based on the measurements of the RF receiver(s) 220 and/or RF sensor(s) 208. In one embodiment, the learned gradient-active and gradient-idle time intervals are stored in computer memory, which can be implemented as any type of volatile or non-volatile (e.g., Flash) memory. The activity of the concurrently operated system 202 may then be synchronized to the MRI system 200 based on the stored MRI pulse sequence retrieved from the memory. This approach allows the RF-sensitive operations to be performed concurrently with the MRI scanning in a subsequent (or a new) MRI pulse sequence without the need to measure, in real time, RF signals originating from the MRI apparatus 200 in order to identify the MRI gradient-active and gradient idle time intervals each time RF-sensitive operations are to be performed.

The dedicated sensor(s) 208 may be made of a wire loop or a solenoid that is sensitive to the MR electromagnetic interference but not to the measuring signals originating from the concurrently operated system 202. The dedicated sensor(s) 208 may be placed inside the MR bore 106 in a location that is sensitive to gradients along each axis but does not interfere with the concurrently operated system 202 for performing RF-sensitive measurements during MR scans. Again, based on the measured RF disturbance resulting from operation of the MRI apparatus 200, the MRI apparatus 200 and the concurrently operated system 202 are synchronized so that the non-RF-sensitive operations are carried out during gradient-active periods (or MR active periods), reserving the quiet times (or gradient-idle times) for RF-sensitive operations.

Figure 3B:
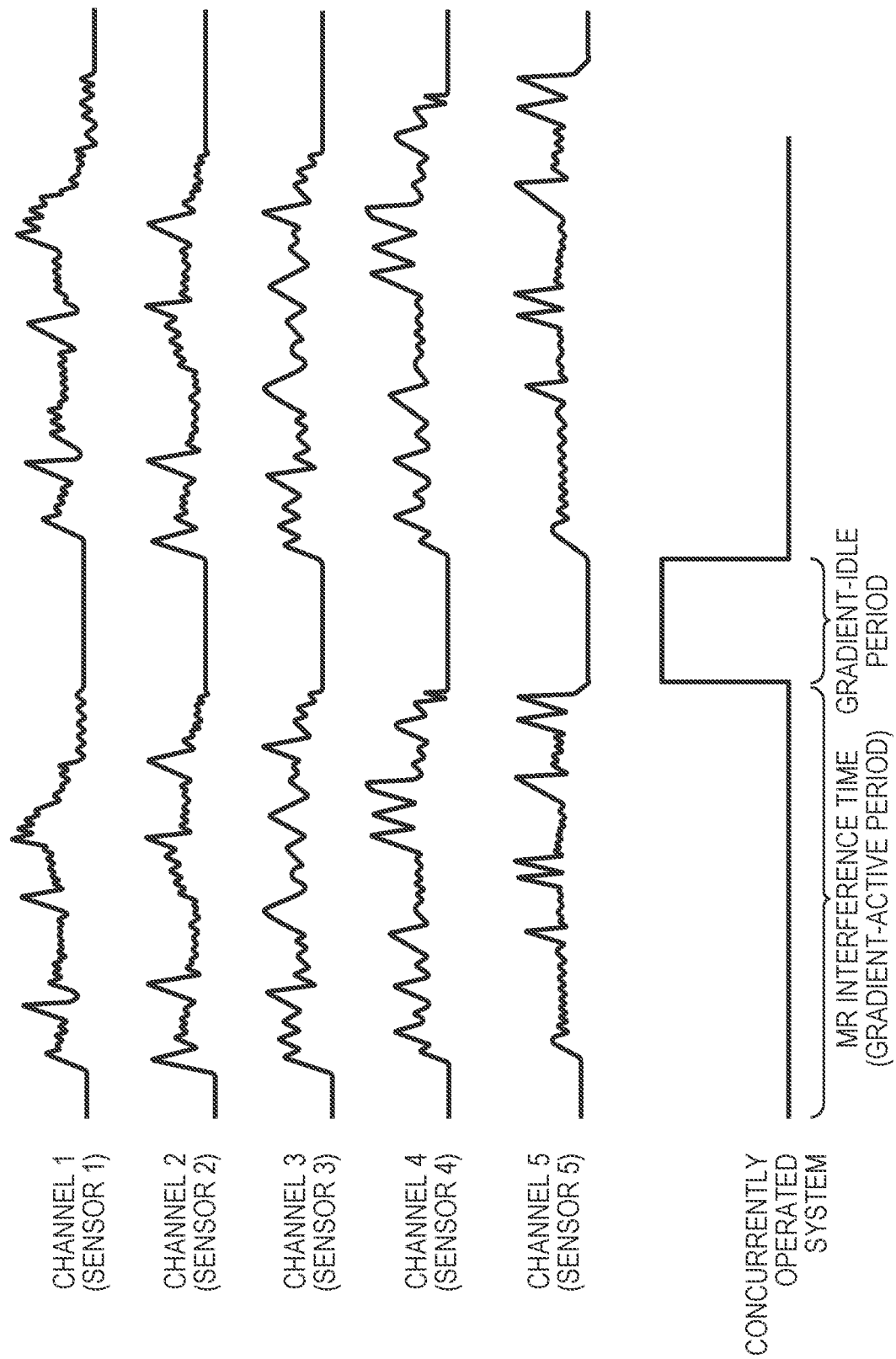
FIG. 3B depicts MR gradient-active periods determined based on a summation of the active-gradient times detected by some individual MR receivers/sensors in accordance with various embodiments of the current invention.

Referring to FIG. 3B, when more than one receiver 220 and/or sensor 208 is simultaneously used to measure the RF signals, each receiver 220 and/or sensor 208 may detect the RF disturbance with a different amplitude and/or phase. In one embodiment, the MR gradient-active periods are defined as a sum (i.e., the union) of the active-gradient times detected by at least some of the individual receivers 220 and/or sensors 208. That is, if the MRI pulse sequence is not available to the controller 216, it can be learned.

In some embodiments, the MRI sequence stops running after it completes, and MR-sensitive operations are performed following the end of one sequence and before the beginning of the next sequence. The next sequence may begin automatically or may be triggered by an external control signal. The concurrently operated system 202 identifies the end of a sequence (e.g., by measuring RF signals generated by the MRI apparatus using the dedicated receiver(s)/sensor(s)), performs the RF-sensitive measurements, and then sends a trigger command to the MRI apparatus indicating completion of the RF-sensitive measurements. The MRI apparatus 200 may then execute the next sequence. This delay may occur between successive sequence or may, depending on the application, may be postponed or staggered so that the MRI sequence is repeated one or more times before the RF-sensitive operation is carried out (i.e., one or more sequence transitions is skipped). The system may also be programmed to perform the RF-sensitive measurements only after certain MRI procedures, for example, only after thermal imaging sequences. External control generally provides a high degree of flexibility in timing MR imaging and RF-sensitive measurements, thereby facilitating time efficiency in the overall procedure.

In general, functionality for synchronizing an MRI apparatus and a concurrently operated system as described above, whether integrated with the controllers of MRI and/or the concurrently operated system or provided by a separate external controller, may be structured in one or more modules implemented in hardware, software, or a combination of both. For embodiments in which the functions are provided as one or more software programs, the programs may be written in any of a number of high level languages such as FORTRAN, PASCAL™, JAVA™, C, C++, C#, BASIC, various scripting languages, and/or HTML. Additionally, the software can be implemented in an assembly language directed to the microprocessor resident on a target computer; for example, the software may be implemented in Intel™ 80x86 assembly language if it is configured to run on an IBM™ PC or PC clone. The software may be embodied on an article of manufacture including, but not limited to, a floppy disk, a jump drive, a hard disk, an optical disk, a magnetic tape, a programmable read-only memory (PROM), an erasable programmable read-only memory (EPROM), electrically erasable programmable read-only memory (EEPROM), field-programmable gate array, or CD-ROM. Embodiments using hardware circuitry may be implemented using, for example, one or more field-programmable gate array (FPGA), complex programmable logic device (CPLD) or application-specific integrated circuit (ASIC) processors.

Figure 4A:
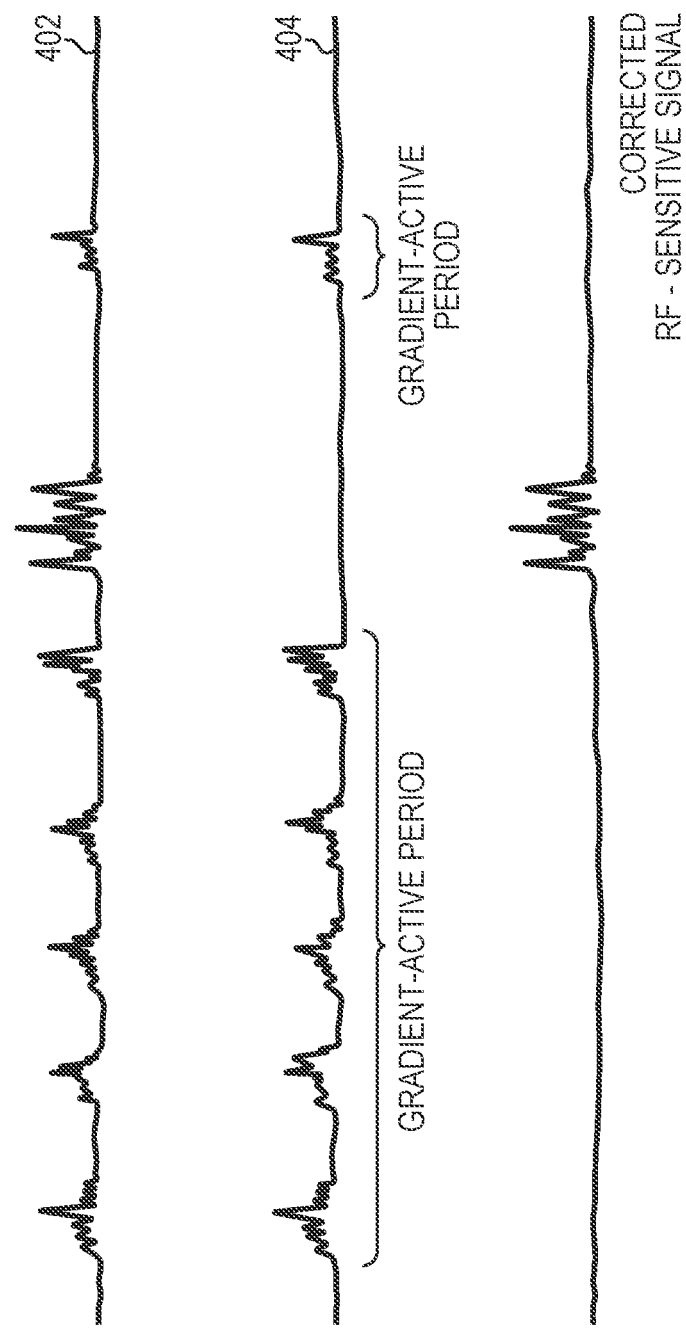
FIGS. 4A-4E depict various approaches for measuring RF-sensitive signals with reduced or eliminated MRI interference in accordance with various embodiments of the current invention.

FIG. 4A illustrates a learning procedure that does not require a "cold" scan as described above. Instead, the concurrently operated system 202 performs the RF-sensitive measurements during the MR gradient-active periods (i.e., "hot scans"); the measured signals 402 include the MR electromagnetic interference. In one embodiment, while both the MRI and concurrently operated systems are active during the hot scans, the dedicated sensors 208 separately, and in parallel, detect the MR interference 404. Because the dedicated sensors 208 are sensitive to the MR electromagnetic interference originating from MRI operations but not to the measured signals from the concurrently operated system 202, signals detected using the dedicated sensors 208 can be used to define the MR gradient-active periods if these are not known to the controller 216 in advance. As described above, the time periods during which the detected RF signals exceed a threshold are defined as gradient-active times, whereas the time periods during which the detected RF signals are below a threshold are defined as gradient-idle times. Accordingly, the RF-sensitive measurements carried out using the concurrently operated system 202 can be corrected by discarding the data measured during the time intervals corresponding to active-gradient periods, which have been learned based on the measurements of the dedicated sensors 208.

Figure 4B:
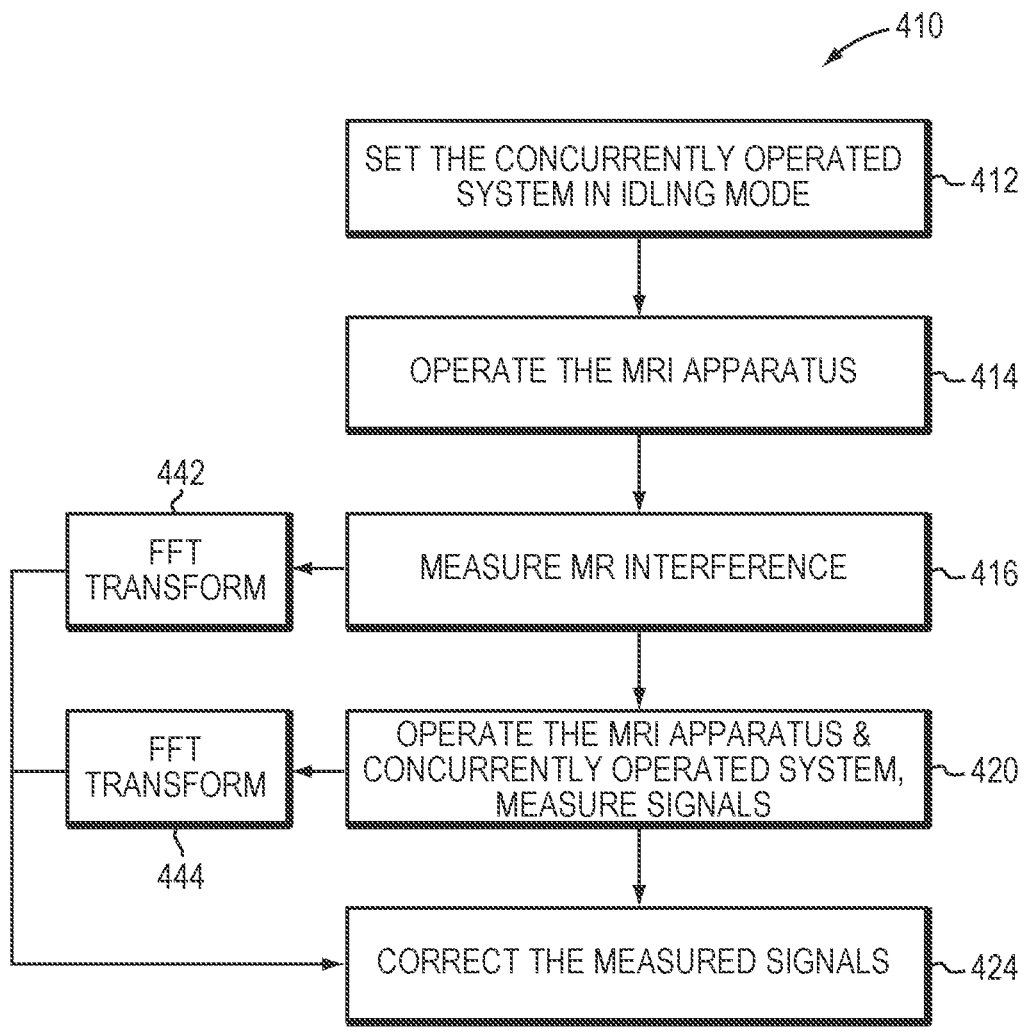
Figure 4C:
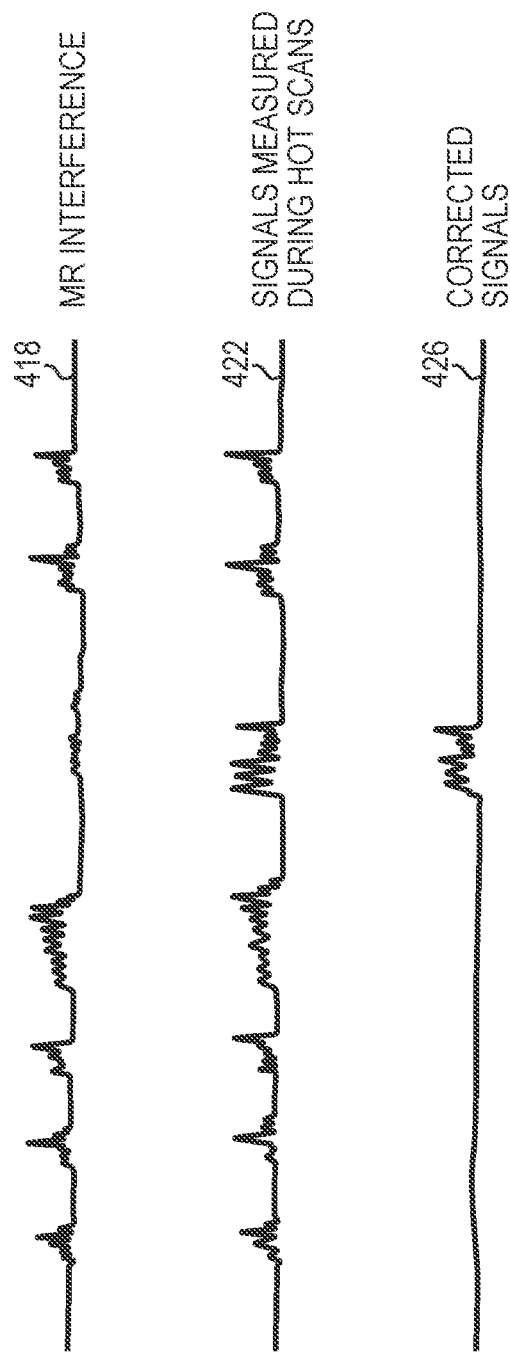

In another embodiment, the signals measured by the concurrently operated system 202 are corrected in accordance with a signal-correction procedure as further described below. FIGS. 4B and 4C depict a signal-correction procedure 410 that allows the MRI apparatus 200 and the concurrently operated system 202 to operate simultaneously—i.e., the MRI apparatus 200 obtain MRI images and the concurrently operated system 202 perform RF-sensitive measurements. In a first step 412, the concurrently operated system 202 is first set in an idling mode—i.e., it is powered on but not activated to transmit energy. For example, if the concurrently operated system 202 is a focused ultrasound system, no ultrasound channels are actively driven to transmit acoustic waves yet the ultrasound channels are ready to receive acoustic signals in the idling mode. In a second step 414, the MRI apparatus 200 is activated and operated in accordance with a normal procedure—i.e., emitting a pulse sequence of magnetic field gradients and RE excitation pulses into the imaging region to cause the patient's tissues to emit MR response signals. As described above, this step is a "cold" scan as the concurrently operated system is inactive during MR scanning. In a third step 416, the MR interference 418 resulting from activations of the MRI apparatus 200 is measured by the detection channels and/or sensors (e.g., cavitation sensors) associated with the concurrently operated system 202; the measured MR interference may be stored in computer memory, which be implemented as any type of volatile or non-volatile (e.g., Flash) memory. In a fourth step 420, both MRI apparatus 200 and concurrently operated system 202 are simultaneously activated (i.e., a "hot" scan), while the detection channels and/or sensors receive signals 422 transmitted thereto. Because the MRI interference 418 is typically an additive, stationary noise with respect to the measured signals, signals 422 detected by the concurrently operated system 202 can be corrected by subtracting the MRI interference measured during the cold scans from the detected signals 422 obtained during the hot scans (in a fifth step 424), based on the temporal locations of the interfering MR pulses learned during the cold scan. This approach thus provides effective corrections 426 to the desired signals measured by the concurrently operated system 202 with no (or at least limited) MRI-caused interference.

Figure 4D:
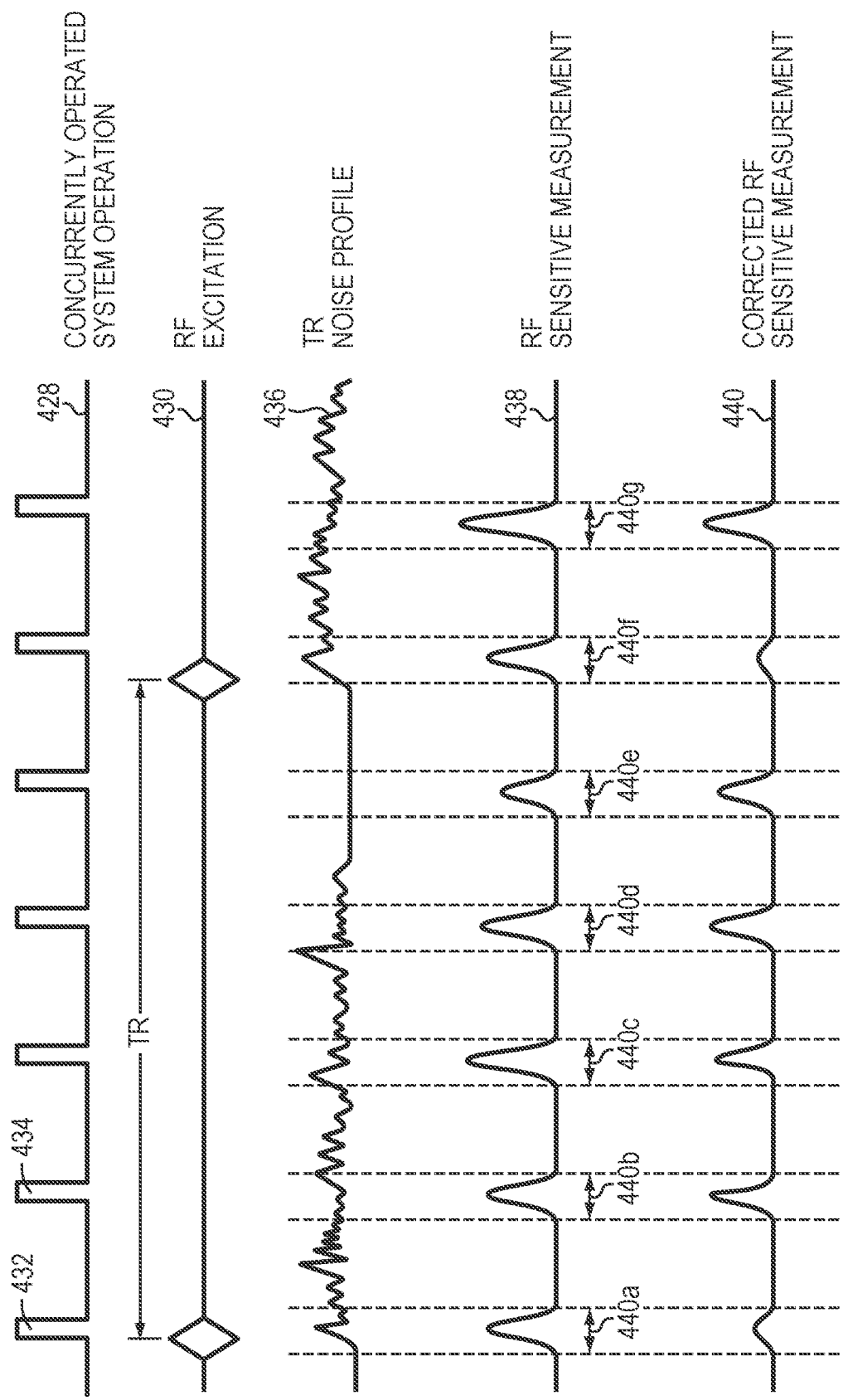

Referring to FIG. 4D, the concurrently operated system 202 may be activated with a period 428 shorter than the repetition time TR 430. For example, the cavitation measuring time may be in the order of 1 ms while the repetition time TR is in the range from 20 to 30 ms. Thus, the cavitation (or other) measurements 428 may not be synchronized with the TRs 430; successive measurement windows 432, 434 can occur during different intervals within each TR and/or successive TRs. In one embodiment, to correct these cavitation signals (or other signals) measured during different time windows, a TR noise profile 436 is first established using the cold scan as described above. Because the MR noise varies throughout the TR duration, the TR noise profile 436 allows the overall MR interference magnitude, which is a function of time during the TR, to be tracked. When the concurrently operated system 202 is activated to perform cavitation (or other RF-sensitive) measurements 438 during a hot scan, the concurrently operated controller 216 can determine the time windows 440a-440g associated with the RF-sensitive measurements and subsequently identify the MR interference levels in the particular measurement windows using the established TR noise profile 436. Accordingly, the measured signal can be corrected by subtracting the identified MR interference noise therefrom. Additionally, the MR interference may be pseudo-stationary for each sequence repetition (or time to repeat (TR)), so that only phases encoded in the gradient amplitudes are changed between the TRs. In some embodiments, the MRI interferences obtained during the cold scans are reduced to a single set of data obtained from, for example, a single cold scan TR, an average of MR interferences in multiple cold scan TRs, or a maximum MR interference in the multiple cold scan TRs. This approach may advantageously reduce the complexity when processing a massive data volume of signal(s) acquired during simultaneous operations of the MRI apparatus and concurrently operated system.

The signal-correction procedure as depicted in FIGS. 4B and 4C may be combined with the learning procedure of the MR gradient-active periods as illustrated in FIG. 4A. For example, at the end of each MR sequence, the controller 216 of the concurrently operated system 202 may correct the RF-sensitive signals measured during hot scans by discarding the data measured during the active-gradient periods as described in FIG. 4A. If, however, the discarded data is above a threshold (e.g., 30% of the acquired data), the controller 216 may start the signal-correction procedure—i.e., subtracting the MR interference measured during the cold scans from the measured RF-sensitive signals obtained during the hot scans—as described in FIGS. 4B and 4C or adjust the RF-sensitive measurements based on the measured magnitude of the MR interference in the subsequent MR sequence(s). In another example, the controller 216 may in real time subtract the MR interference from the received RF-sensitive signals. If, however, the controller 216 determines that the MR noise obtained during cold scans, is above a threshold that may result in unreliable RF-sensitive measurements, the controller 216 may, again, discard or reject the measured RF-sensitive signals during the high-noise time period(s).

Figure 4E:
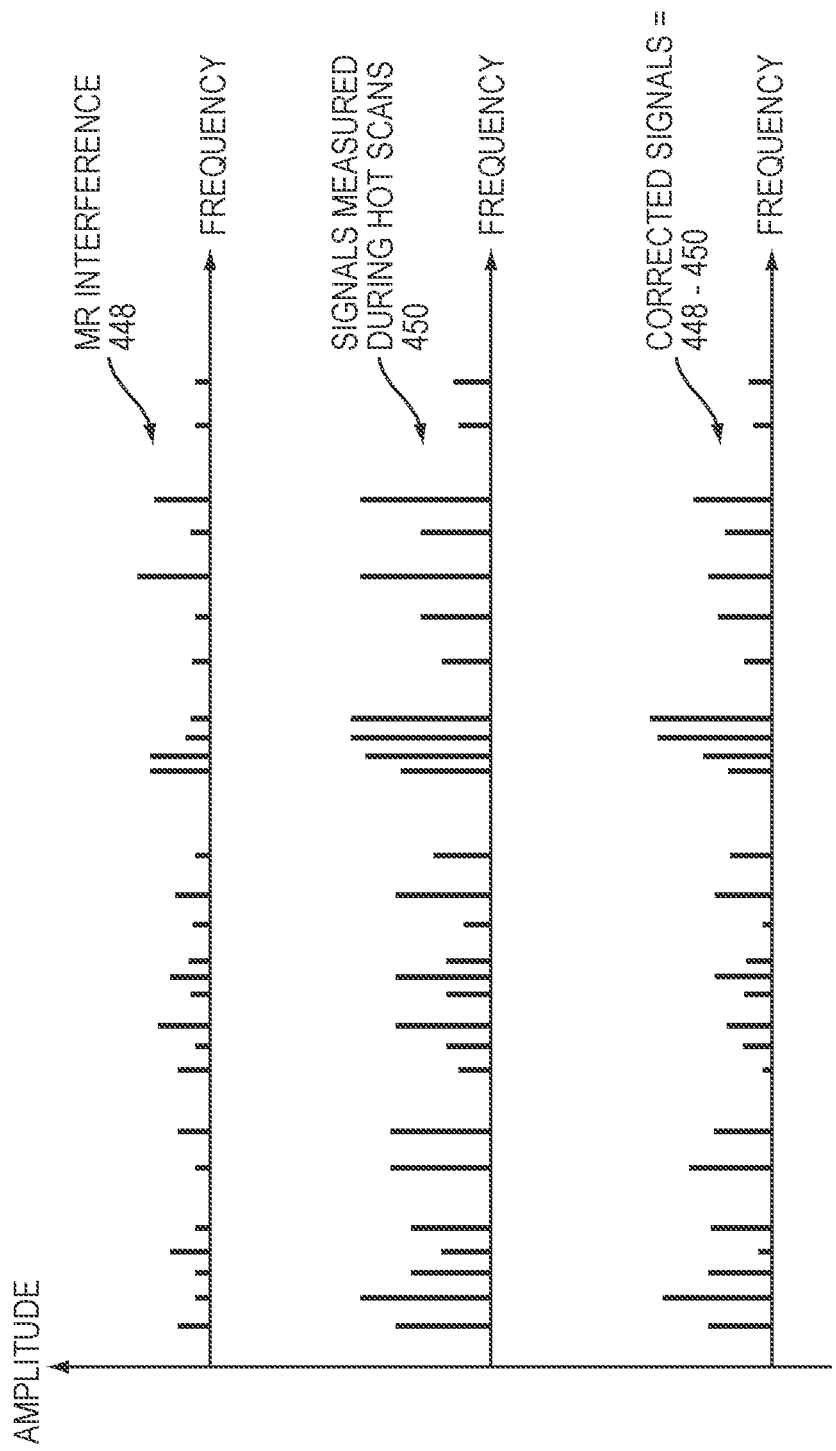

Referring to FIG. 4E, in various embodiments, the MR interference noise measured during the cold scans and signals measured during the hot scans are converted into signals 448, 450, respectively, in the frequency domain using, e.g., a Fast Fourier Transform (FFT) (steps 442 and 444, respectively, as depicted in FIG. 4B). Subtraction of the MRI interference noise 448 from the measured signal(s) 450 can be then performed by directly subtracting the magnitude of the converted signals at each frequency in the spectrum. This is particularly useful when the measured signal(s) of the concurrently operated system are insensitive to the phase measurements (e.g., cavitation measurements in focused ultrasound) and avoids the need to accurately synchronize the operations of MRI scanning and the concurrently operated system.

In some embodiments, the synchronization and correction approaches described above are used in conjunction with shielding, signal filtering, and/or processing. For example, if the synchronization approach is combined with shielding, there is generally a trade-off between the amount of shielding used and the maximum acceptable noise. The less shielding is used, the quieter the gradients need to be to avoid undesired interference between the MRI system and the ultrasound (or other concurrently operated) system. If the signal correction approach is combined with shielding, the more shielding is used, the less correction is required. Noise reductions due to shielding depend on the particular material used (e.g., iron, copper, or nickel) as well as on the frequency range of interest, and can readily be ascertained based on graphs and tabulations of absorption and reflection coefficients that are available in the literature. For example, at frequencies of around 1 MHz, a 3 mm thick iron shield reduces the noise by about 100 dB. For a given maximum acceptable noise level (which, in turn, depends on the signal filtering and processing capabilities of the system), the maximum allowable gradients can be computed based on the noise reduction achieved by shielding.

Although the present invention has been described with reference to an ultrasound transducer system and other specific details, it is not intended that such details should be regarded as limitations upon the scope of the invention. For example, systems and methods for synchronizing MR imaging with treatment modalities other than focused ultrasound therapy that include RF-sensitive operations are also included within the scope of the invention. Moreover, the terms "MR interference," "MR interference noise," "MR noise," "RF noise," and "RF disturbance" are used herein interchangeably. Further, it is to be understood that the features of the various embodiments described herein are not necessarily mutually exclusive and can exist in various combinations and permutations, even if such combinations or permutations are not made express herein, without departing from the spirit and scope of the invention. In fact, variations, modifications, and other implementations of what is described herein will occur to those of ordinary skill in the art without departing from the spirit and the scope of the invention.

What is claimed is:

1. A method of performing magnetic resonance (MR) imaging of an anatomic region in conjunction with an ultrasound measurement of the region using an ultrasound system, the method comprising the steps of:
   simultaneously performing an MR scan sequence including MR pulses and the ultrasound measurement;
   recording the ultrasound measurement as the ultrasound measurement is made;
   detecting time intervals during the MR scan sequence when a radio frequency (RF) level is sufficient to interfere with the ultrasound measurement; and
   discarding the ultrasound measurement performed within the detected time intervals and retaining only the ultrasound measurement performed outside the detected time intervals.

2. The method of claim 1, wherein the detecting step is performed by the ultrasound system.

3. The method of claim 1, wherein the detecting step is performed by at least one dedicated sensor outside the ultrasound system.

4. A system for performing magnetic resonance (MR) imaging of an anatomic region in conjunction with an ultrasound measurement of the region, the system comprising:
   an MR imaging apparatus for imaging the anatomic region;
   an ultrasound system for performing the ultrasound measurement; and
   a controller in communication with the MR imaging apparatus and the ultrasound system, the controller being configured to:
   simultaneously perform an MR scan sequence including MR pulses and the ultrasound measurement;
   record the ultrasound measurement as the ultrasound measurement is made;
   determine time intervals during the MR scan sequence when a radio frequency (RF) level is sufficient to interfere with the ultrasound measurement; and
   discard the ultrasound measurement performed within the determined time intervals and retain only the ultrasound measurement performed outside the determined time intervals.

5. The system of claim 4, wherein the controller is implemented in the ultrasound system and the determination of the intervals is performed by the ultrasound system.

6. The system of claim 4, wherein the determination of the intervals is performed by at least one dedicated sensor outside the ultrasound system.

7. The system of claim 4, wherein the ultrasound system comprises at least one of a phased-array ultrasound transducer system, an ultrasound imaging probe, or a cavitation sensor.

* * * * *